United States Patent [19]
Naccache et al.

[11] Patent Number: 6,069,128
[45] Date of Patent: May 30, 2000

[54] TRANSIENTLY MEMBRANE-PERMEABLE DERIVATIVES CONVERTED INTRACELLULARLY INTO ACTIVE PEPTIDES

[75] Inventors: Paul H. Naccache, Sillery, Canada; Bassam B. Damaj, Laurenceville, N.J.; Shaun R. McColl, Myrtle Bank, Australia

[73] Assignee: Université Laval, Québec, Canada

[21] Appl. No.: 09/114,478

[22] Filed: Jul. 13, 1998

Related U.S. Application Data

[63] Continuation-in-part of application No. 08/782,277, Jan. 13, 1997, abandoned.

[51] Int. Cl.[7] .................................................. A61K 38/00
[52] U.S. Cl. .................... 514/15; 514/2; 514/14; 514/16; 514/17; 514/885; 514/886; 514/887
[58] Field of Search ..................... 514/2, 14, 15, 514/16, 17, 885, 886, 887

[56] References Cited

U.S. PATENT DOCUMENTS

| | | | |
|---|---|---|---|
| 5,332,802 | 7/1994 | Kelman et al. | 530/356 |
| 5,350,681 | 9/1994 | Iacobucci et al. | 435/68.1 |
| 5,607,691 | 3/1997 | Hale et al. | 424/449 |

FOREIGN PATENT DOCUMENTS

| | | |
|---|---|---|
| 6100595 | 4/1994 | Japan. |
| 9311784 | 6/1993 | WIPO. |
| WO/94/23724 | 10/1994 | WIPO. |
| 9428931 | 12/1994 | WIPO. |

*Primary Examiner*—Leon B. Lankford, Jr.
*Assistant Examiner*—Christopher R. Tate
*Attorney, Agent, or Firm*—Swabey Ogilvy Renault; France Côté

[57] ABSTRACT

The present invention relates to membrane-permeable peptides which are intracellular agonists and/or antagonists of chemotactic factor receptors rendered hydrophobic through acylation and acetoxymethylation of their amine and acid functional groups. The modified peptides of the present invention are loaded into cells. The acetoxymethyl esters are cleaved by non-specific esterases rendering the peptides active in the intracellular compartments of the cells. The effects of the introduction of transformed specific peptides corresponding to intracellular regions common to the major chemokine receptors are illustrated. These peptides completely inhibited chemotactic factor and chemokine-induced calcium mobilization. Furthermore, leukocytes of mice intravenously injected with these peptides failed to migrate towards chemokines(IL-8).

3 Claims, 6 Drawing Sheets

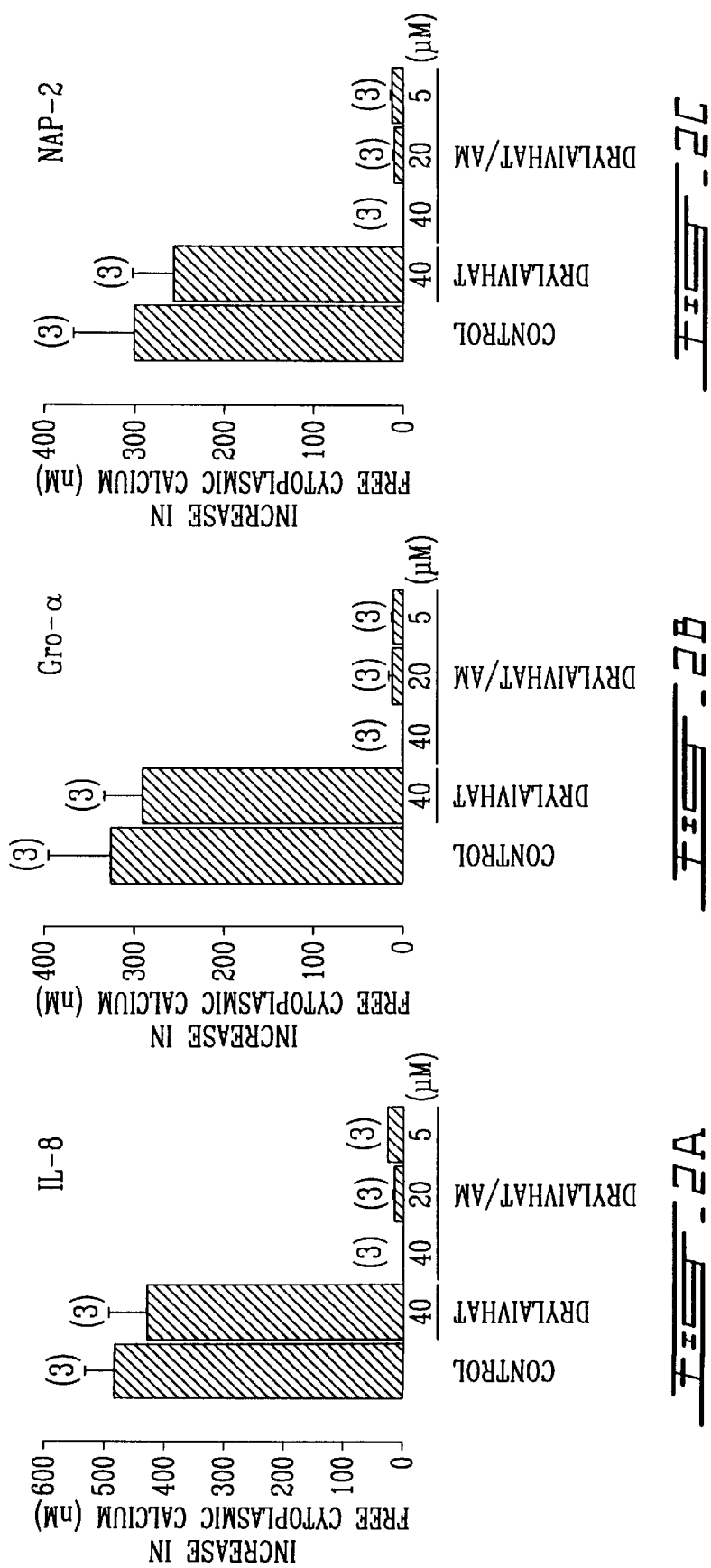

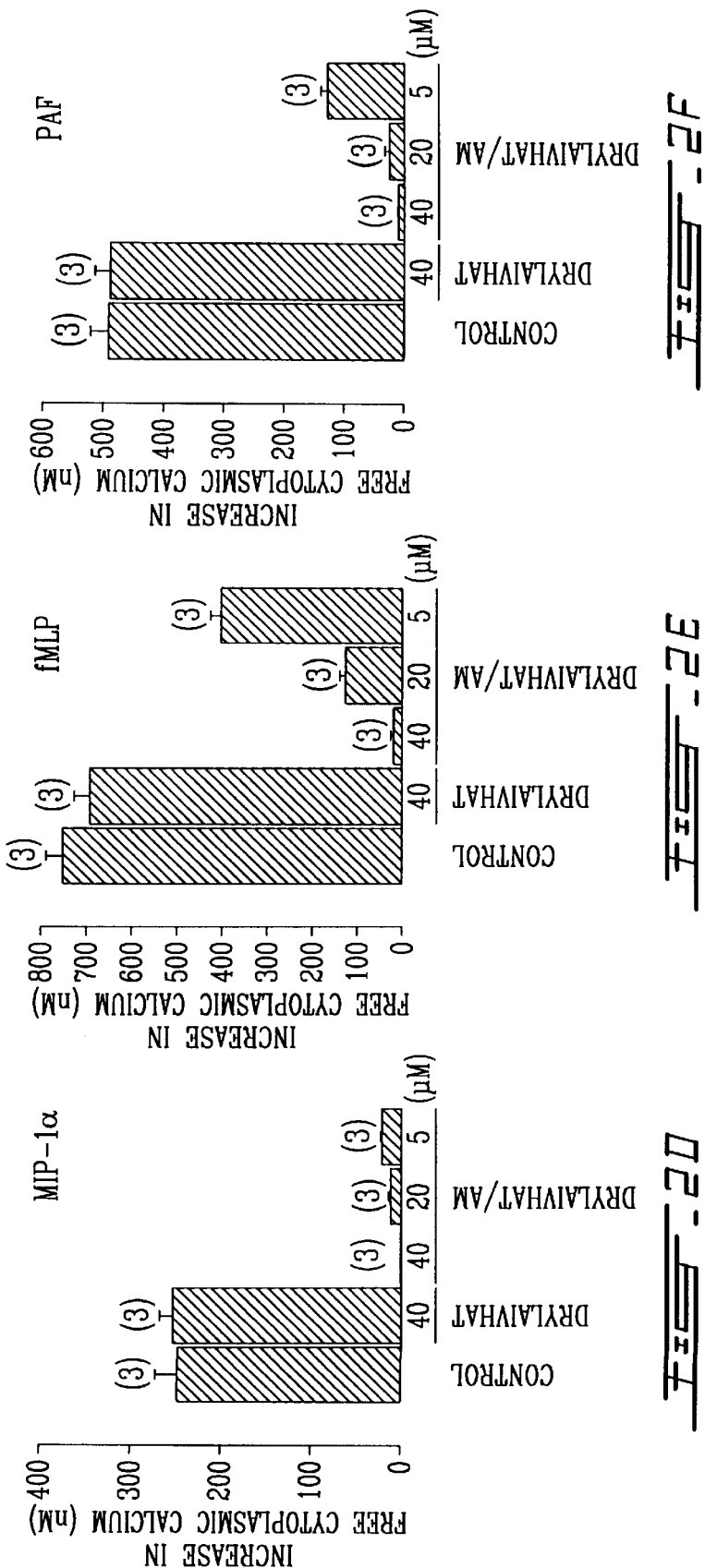

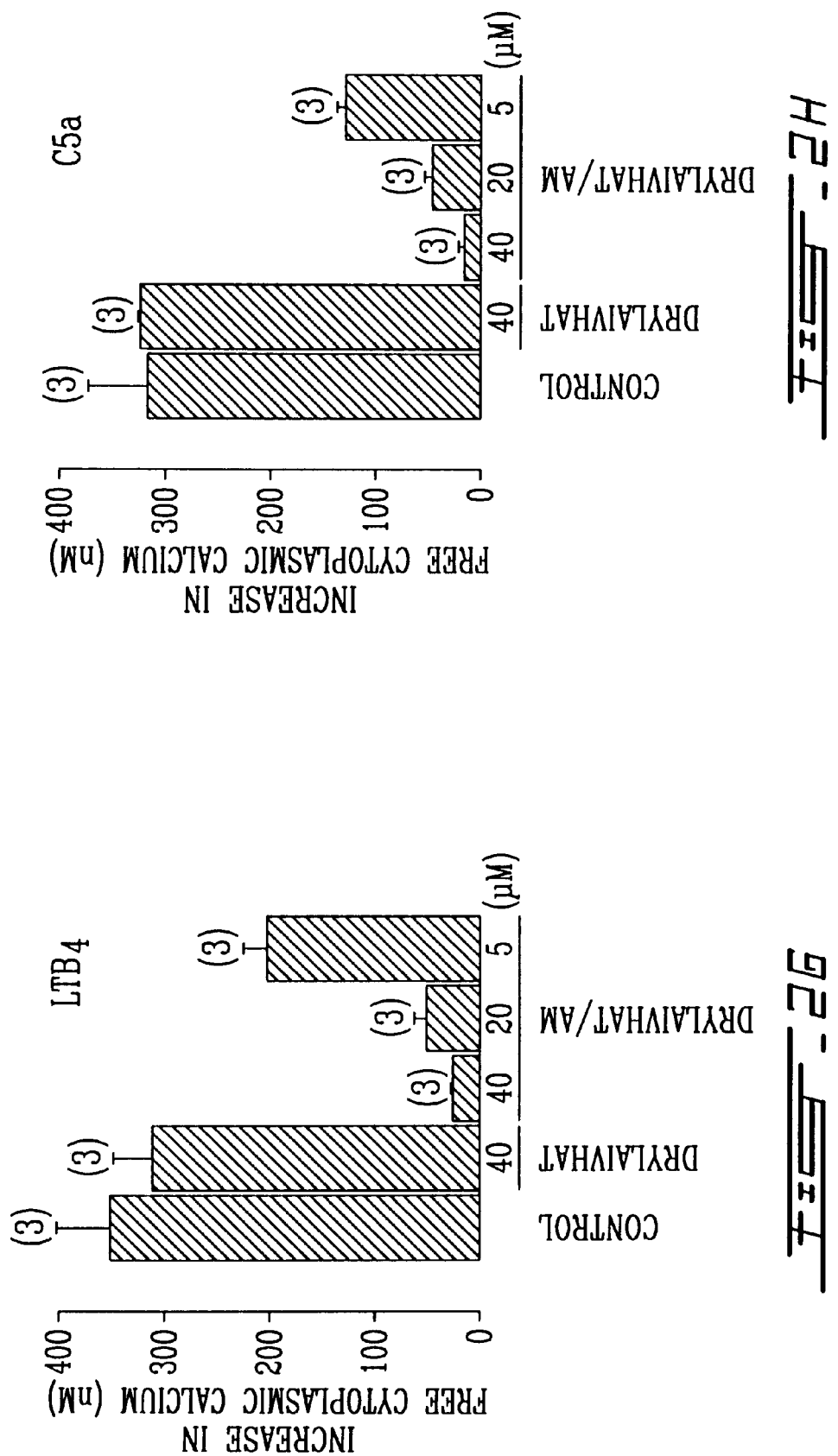

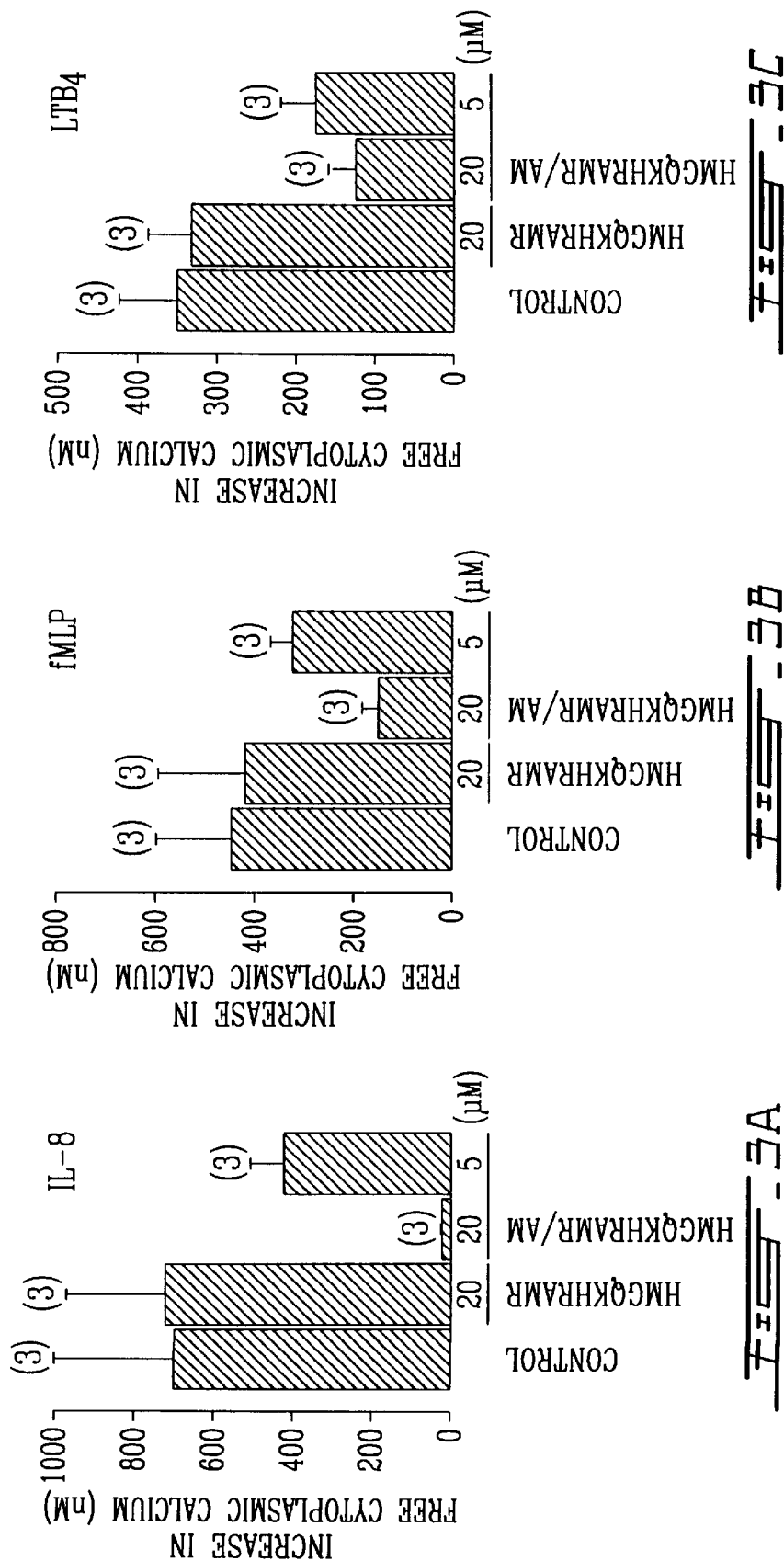

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1:

Asp Arg Tyr Leu Ala Ile Val His Ala Thr
1               5                   10

(2) INFORMATION FOR SEQ ID NO:2:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

His Met Gly Gln Lys His Arg Ala Met Arg
1               5                   10

TRANSIENTLY MEMBRANE-PERMEABLE DERIVATIVES CONVERTED INTRACELLULARLY INTO ACTIVE PEPTIDES

RELATED APPLICATIONS

This is a continuation-in-part of U.S. Ser. No. 08/782,277 filed Jan. 13, 1997, now abandoned. The entire contents of application Ser. No. 08/782,277 are hereby incorporated by reference.

BACKGROUND OF THE INVENTION (a) Field of the Invention

The invention relates in general to biologically important intracellular agonists and antagonists such as peptides and other proteins. More specifically, the present invention relates to modifying hydrophilic peptides corresponding to intracellular regions of receptors and effector proteins to form membrane-permeable hydrophobic derivatives enabling them to cross cell barriers without disrupting the cell membrane to interact with their intracellular targets.

(b) Description of Prior Art

Intracellular agonists are, by definition, molecules that, when introduced into cells, will take the place of endogenous ones and specifically activate distinct intracellular signalling pathways such as G-protein activation, adenylyl cyclases, and phospholipases. Intracellular antagonists are, on the other hand, molecules that oppose the effects of cell behaviour to certain stimuli. Most of the published studies have concentrated on the use of extracellular antagonists to inhibit or block induced cell activation both in vivo and in vitro.

Uncontrolled cell activation can be a cause of disease and inflammation and constitutes one of the manifestations of such diseases. Inflammation is a complex process that involves the action of a variety of factors such as chemokines and cytokines. Pro-inflammatory chemotactic factors and chemokines such as fMLP, C5a, IL-8, NAP-2, Go-, PAF, LTB4, and MIP-1 are essential in initiating the inflammatory cascade which may result in cell and tissue damage. Most of these factors and their receptors are well-characterized at the biological and molecular levels. Their interaction with inflammatory cells (neutrophils, monocytes/macrophages, lymphocytes) leads to the initiation of the activation of a complex array of intracellular biochemical events, several of which have been described in detail.

Earliest signalling events in chemokine activation is G-protein coupling to the intracellular loops of surface receptors activated by hormones and peptides. G-proteins (guanine nucleotide binding proteins) are integral part of regulating mechanisms that operate in all human cells. Impairing G proteins function can affect a cell's response to hormone or chemotactic peptides signals e.g. by interfering with intracellular metabolic pathways. G-proteins act as essential parts of transducing mechanisms by which hormones and neurotransmitters convey their signals through the plasma membrane of the cell and thus elicit appropriate intracellular responses leading to cell function. These signal transducing mechanisms comprise three distinct components:

1-a receptor protein with an extracellular binding site specific for a given agonist or hormone;

2-a membrane-bound effector protein that when activated catalyzes the formation or facilitates the transport of an intracellular second messenger, such as adenyl cyclase which converts ATP to cyclic AMP (cAMP); and 3-a protein which functions as a communicator between these two.

G-proteins fulfil this function as communicator between receptor and effector proteins in the generation of intracellular responses to extracellular hormones and agonists. This knowledge facilitates the design of small peptides (>5 amino acids) directed against regions of intracellular proteins which, once introduced into the cells, can specifically and selectively interact with their targets to alter (enhance or inhibit) cell activation. This can lead to the development of novel therapeutic strategies based on the use of peptides directed against intracellular regions of proteins.

In International Patent Application published under No. WO/94/23724 on Oct. 27, 1994 in the name of The Regents of the University of California, there is described acyloxyalkyl esters of phosphate-containing second messengers which are capable of permeating cell membranes. Once inside the cell, the esters derivatives undergo enzymatic conversion to the biologically active form of the second messenger. The main disadvantage of this method is its specificity towards a single signalling pathway.

The use of peptides as extracellular antagonists is widely used for many therapeutic drugs. There are three descriptions of such reagents discussed in U.S. Pat. Nos. 5,607,691 (Hale et al.), 5,350,681 (Iacobucci et al.), and 5,332,802 (Kelman et al.).

Hale et al. discusses the use of peptide modifiers and chemical linkers to improve the transport and delivery of pharmaceutical agents (including peptides to extracellular domains of receptors and do not include peptides directed towards intracellular parts of transmembrane and intracellular proteins.

Kelman et al. and Iacobucci et al. support Hale et al. by disclosing some chemical modification of amine and carboxyl groups on peptides directed against extracellular receptors. The list of peptides listed in these patents include only peptide ligands such as chemokines, peptidic agonist and/or antagonist against extracellular receptors. These patents however has never taught any modification for intracellular peptides that would make it obvious to any skilled in the art to carry out. Also, their suggested modification do not make the peptides claimed in their patent hydrophobic enough to cross the membrane efficiently. Another important point in the modification taught by Kelman et al. and Iacobucci et al. is that the modification of the peptide is not reversible and would be inactive against intracellular target proteins.

On the other hand, little success has been reported with the use of peptides as intracellular agonists or antagonists due to the hydrophilic nature of proteins and amino acids which renders them incapable of crossing cell membranes due to low interaction with the membrane lipids.

It would be highly desirable to be provided with a new method that enables the modification of low molecular weight molecules (peptides larger than 5 amino acids) from a hydrophilic non-permeable to a completely hydrophobic membrane-permeable form.

SUMMARY OF THE INVENTION

One aim of the present invention is to provide a new method that enables the modification of low molecular weight molecules (peptides larger than 5 amino acids) from a hydrophilic non-permeable to a completely hydrophobic membrane-permeable form without affecting their activity. This method is moving away from addition of linkers or a permanent chemical modifier which by increasing the hydrophobicity of the peptide transformed, changes its nature and eliminates its activity.

The present invention introduces the concept of the use of hydrophobic cell-permeant peptides as modifiers of cellular responsiveness. The invention involves the transformation of otherwise hydrophilic non-permeant peptides into their acetoxymethyl ester (AM)-counterparts which can diffuse into the cells, be trapped there, and react with their intracellular targets. The advantage of this method is the use of endogenous intracellular esterases to cleave the AM moiety from the peptides and thus reverting them to their original active form.

The chosen peptides which are ideal when they exceed 5 amino acids (aa) in length and are directed against important parts of intracellular proteins should contain at least one primary amine and one carboxylic acid. Those peptides are dissolved in dimethylformamide (DMF), diisopropylethylamine is added followed by acetic anhydride. Acetoxymethyl bromide is added and the mixture is continuously stirred overnight at room temperature. Reaction mixture is diluted with ethyl acetate and washed with water. The ethyl acetate layer is evaporated to dryness and dissolved in an appropriate HPLC buffer followed by an HPLC purification step. This HPLC purified transformed peptides are >98% pure. The purified peptide are than diluted in DMSO for in vitro testing and polythelyne glycol or cyclodextrane for in vivo animal testing.

The acetoxymethyl ester(AM)-membrane-permeable derivative peptides in accordance with a preferred embodiment of the present invention constitute an efficient tool to make intracellular agonists and/or antagonists. As an example, IL-8RA specific peptides were transformed with the above detailed chemistry and were introduced inside the cell to block in vitro and in vivo chemokine-induced cellular activation.

In accordance with the present invention there is provided a method for preparing transient hydrophobic membrane-permeable peptide derivative of more than 5 amino acids corresponding to a region of transmembrane or intracellular proteins. The peptide derivative has an original active form and a transient modified inactive form for entering into a cell without disrupting the cell membrane and is converted by esterases to the original active form inside the cell. The method comprises the steps of:

a) converting temporary primary amines of a peptide to acetamides, thereby rendering the peptide so-converted less water-soluble;

b) converting temporary carboxylic acid and alcohol groups of the peptide obtained from step a) to esters; and c) dissolving the peptide obtained from step b) in cyclodextrane or polyethylene glycol which are pharmaceutically acceptable for administration.

Preferably, the method of the present invention further comprises before step c) the step of i) purifying the peptide obtained from step b) by HPLC.

The step a) may be effected by subjecting the peptide to acetic anhydride or acetyl chloride with a base.

The step b) may effected by subjecting the peptide to at least one reagent, which include, without limitation, acetoxymethyl bromide, diazomethane, and methyl iodide.

In accordance with the present invention there is provided a membrane-permeable peptide larger than 5 amino acids and corresponding to a region of transmembrane or intracellular proteins. The peptide has a transient modified inactive form for entering into a cell without disrupting the cell membrane and is converted by esterases and peptidases to an original active form inside the cell. The peptide comprises primary amine groups modified to acetamides and carboxylic acid and alcohol groups modified to acetoxymethyl esters, wherein the esterases cleave the acetoxymethyl moiety of the acetoxymethyl esters thereby converting the transient modified inactive form of the peptide to the original active form.

In accordance with the present invention there is also provided a pharmaceutical composition comprising a therapeutically effective amount of a peptide as defined above in association with a pharmaceutically acceptable carrier.

In accordance with the present invention there is also provided a method of treatment of a disease selected from the group consisting of inflammatory diseases, inflammation, arthritis, AIDS, auto-immune diseases, hypersensitivity, viral infections, and cancer, which comprises administering a pharmaceutical composition as defined above.

Further in accordance with the present invention there is provided an acetoxymethyl ester of a peptide as set forth in SEQ ID NO:1 or SEQ ID NO:2, or a derivative of the peptide having a same inhibitory activity as the peptide to specifically block interleukin-8 related diseases such as adult respiratory disease syndrome (ARDS) or non-specific inflammation related diseases.

In accordance with the present, the following abbreviations are used:

AM: Acetoxymethyl esters;

fMLP: formyl Met-Leu-Phe;

IL-8: Interleukin 8;

NAP-2: Neutrophil activating peptide 2;

Gro-: Melanocyte growth-stimulatory activity;

MIP-1: Macrophage inflammatory peptide 1-;

PAF: Platelet activating factor;

C5a: the small fragment of the 5th component of complement;

DMF: Dimethylformamide; and

LTB4: Leukotriene B4.

ARDS: Adult respiratory disease syndrome.

BRIEF DESCRIPTION OF THE DRAWINGS

FIG. 2 illustrates the effect of a peptide derived from the second intracellular loop of the interleukin 8 type A receptor (DRYLAIVHAT) on the mobilization of calcium induced by chemotactic factors and chemokines;

FIG. 3 illustrates the effect of a peptide derived from the third intracellular loop of the interleukin 8 type A receptor (HMGQKHRAMR) on the mobilization of calcium induced by chemotactic factors and chemokines.

DETAILED DESCRIPTION OF THE INVENTION

Figure 1:
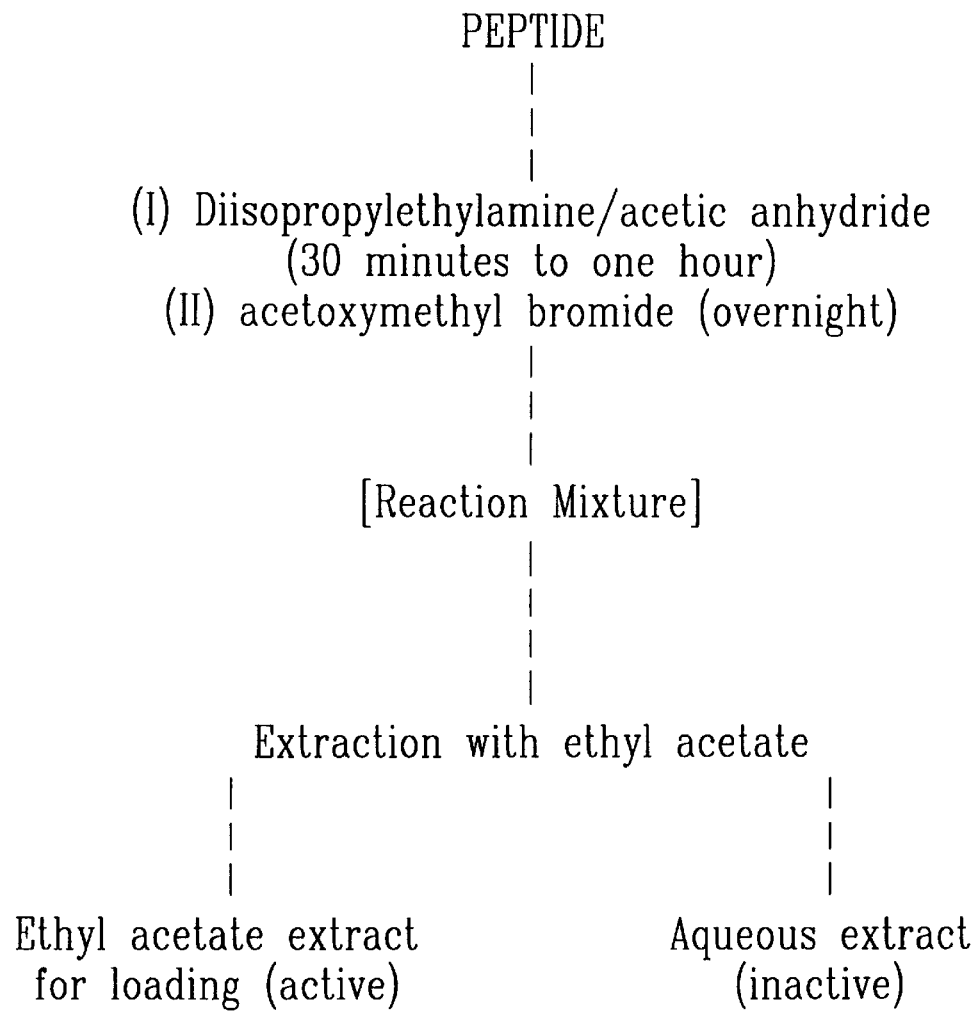
FIG. 1 illustrates a reaction scheme for the transformation of peptides into membrane-permeable derivatives in accordance with the present invention.

All patents, patent applications, and publications referred to herein are hereby incorporated by reference in their entirety. In case of conflict in description or terminology, the present application establishes the following definitions:

"peptides" as used here in refer to peptides of 5–15 aa in length corresponding to hydrophilic parts of intracellular or transmembrane proteins.

"cellular mechanisms" as used here to refer to intracellular signalling pathways such as G-proteins coupling, subsequent enzyme activation (cyclases, cAMP, phospholipases, protein kinases, and gene transcription enzymes) leading to cellular functions and includes second messenger responses.

"native peptides" as used here in refer to peptides in their hydrophilic non-transformed form.

"membrane-permeable peptides or derivatives" as used herein to refer to an ester- or an acetamide-peptide.

Rendering compounds hydrophobic for non-invasive loading is used routinely in studies involving ionic indicators. These non-hydrophobic compounds, like most polar compounds have various carboxylic acid groups which make them hydrophilic in physiological buffers and hence incapable of entering the cells. The carboxylic acids can however be converted into esters for non-invasive loading. The ester of choice is now acetoxymethyl ester because of the speed with which it is hydrolyzed by non-specific esterases inside the cell. The reagent used in the conversion of carboxylic acid to presently acetoxymethyl ester is acetoxymethyl bromide, which is also capable of reacting also with amine and hydroxyl groups which are constituents of most peptides.

In this method primary amines are converted to acetamides with acetic anhydride and base to prevent possible -quaternization of the amines which would render the sample water-soluble. All carboxylic acid and alcohol groups are then converted to esters with acetoxymethyl bromide. The resulting peptide usually dissolves in ethyl acetate and in this form, it can be loaded into cells or used in animal studies. The original form of the peptide is restored by hydrolysis of the esters by cellular esterases.

The modified peptides or membrane-permeable derivatives of the present invention may be used as intracellular agonists or antagonists.

The membrane-permeable derivatives of the present invention are ester-derived peptides which have a neutral charge and can permeate the cell membrane without disrupting the cell membrane. Once inside the cell, the ester groups linked to the derived peptides are cleared by non-specific esterases thereby converting the peptides to their original active form.

There are numerous potential applications of membrane-permeable derivatives of the present invention. Among others, these include the use of such membrane-permeable derivatives derived from the active or regulatory sites of various enzymes including protein kinases, such as protein kinase A, C, MAP kinase, MEK, MLCK, phospholipases (PLC, PLD, PLA), other metabolic enzymes, and the protein-protein interaction sites or domains of signalling molecules such as adapter and anchoring proteins (SH2, SH3, and PH domains). These peptides may be used to stimulate and/or inhibit various elements of the signal transduction pathways leading to a variety of cellular responses such as locomotion, secretion, gene expression, cell growth and division. Finally, antibodies (or their F(ab')$_2$ fragments) could also be similarly modified to be able to penetrate cells.

The membrane-permeable derivatives of the present invention may be used as part of or as a base for therapeutic drugs in the treatment of diseases such as arthritis, auto-immune diseases and hypersensitivity, inflammatory diseases, allergic reactions, viral infections and cancer.

Peptide Derivative Preparation

In accordance with one embodiment of the present invention, specific peptides corresponding to intracellular regions (DRYLAIVHAT and HMGQKHRAMR) common to the major chemokine receptors were transformed to hydrophobic derivatives and they were incubated with leukocytes. Once inside the cells, they are trapped following their de-esterification by cytoplasmic esterases. This enables them to accumulate at high concentrations inside the cells. Under these conditions, they inhibit chemotactic factor and chemokine-induced calcium mobilization. Furthermore, leukocytes of mice intravenously injected with these AM-peptides failed to migrate into tissues in the presence of a chemotactic factor (IL-8) as compared to the controls.

The peptide derivatives synthesized to exemplify the present invention were >98% pure as tested by HPLC.

Two (2) mg of each peptide were dissolved in DMF (500 $\mu$l). This was followed by the addition of 50 $\mu$l of acetic anhydride and 300 $\mu$l of ethyldiethylpropylamine. The solution was stirred for 1 hour. Three hundreds (300) $\mu$l of diazomethane or 150 ul of acetoxymethyl bromide or 300 $\mu$l of methyl iodide was added for an overnight incubation with stirring. The solution was then diluted with 50 $\mu$l of ethyl acetate and 25 $\mu$l of water followed by the addition of dry Na-sulfate, and then filtered. The ethyl acetate layer was evaporated to dryness under vacuum. The ester form of the peptides recovered from the ethyl acetate layer was dissolved in an appropriate HPLC buffer and subjected to additional HPLC run, after which the fraction of the transformed peptides collected was >98% pure. The collected fraction of the pure tranformed peptides was dryed under vaccum and redisolved either in DMSO for in vitro use or in cyclodextrane or polyethylene glycol for in vivo animal use.

Testing of Compounds and their uses

The ester-derived peptides were tested for antagonist activity in one in vitro activation assays and one in vivo assay, namely, the increase in free cytoplasmic calcium and the inhibition of leukocyte migration in mice.

The increase in the level of free cytoplasmic calcium is a direct signal of the occupation of the receptor targeted and its activation by coupling to membrane effector systems. The inhibition of leukocyte infiltration constitutes an in vivo assay in which we test the ability of the compounds to block the migration of leukocytes towards a chemotactic factor (IL-8) in order to evaluate their potential use as anti-inflammatory in humans.

In order to evaluate the role of this new generation of peptides, we have chosen the measurement of intracellular free calcium as an index of intracellular activation and leukocyte migration as a measure of in vivo activation. Two IL-8RA specific peptides (DRYLAIVHAT and HMGQKHRAMR) were chosen on the basis of their previously described action to block chemokine-induced cell activation.

In the first series of experiments, we pre-incubated human neutrophils with various concentrations of the peptides (native or modified) and monitored their ability to block the mobilization of calcium induced by a variety of chemotactic factors and chemokines.

As shown in FIGS. 2 and 3, the AM/transformed peptides completely ablated the stimulated mobilization of calcium whereas in their native form, they were without any detectable inhibitory effects. This inhibition clearly demonstrates that the transformed peptides successfully crossed the cell membranes and inhibited the activation of the cells by the agonists tested.

In FIG. 2, the chemotactic factors were all used at $10^{-7}$M. The peak increase in cytoplasmic free calcium induced by the indicated agonists is shown. The peptides (native or transformed) were incubated for 30 min. at 37° C. at the indicated concentrations with the cells prior to stimulation. The basal calcium levels were 150±25 nM and the increases in calcium represent the differences between the basal and the peak levels of the cytoplasmic concentrations of calcium reached upon stimulation. The data represent the mean ±SEM of the number of experiments indicated in parenthesis.

In FIG. 3, the chemotactic factors were all used at $10^{-7}$M. The peak increase in cytoplasmic free calcium induced by the indicated agonists is shown. The peptides (native or transformed) were incubated for 30 min. at 37° C. at the indicated concentrations with the cells prior to stimulation. The basal calcium levels were 150±25 nM and the increases in calcium represent the differences between the basal and the peak levels of the cytoplasmic concentrations of calcium reached upon stimulation. The data represent the mean ±SEM of the number of experiments indicated in parenthesis.

In the second series of experiments, inhibition of leukocyte migration in BALBc mice was chosen as an in vivo assay as a first step towards the use of the modified peptides in humans. 100 ug of the DRYLAIVHAT/AM peptide, diluted in cyclodextrane or polythelene glycol, was injected intravenously in the tails of BALBc mice one hour prior to the subdermal injection of IL-8. In the presence of the modified peptide, leukocyte migration was inhibited when compared to the migration observed in untreated animals (FIG. 4).

Figure 4:
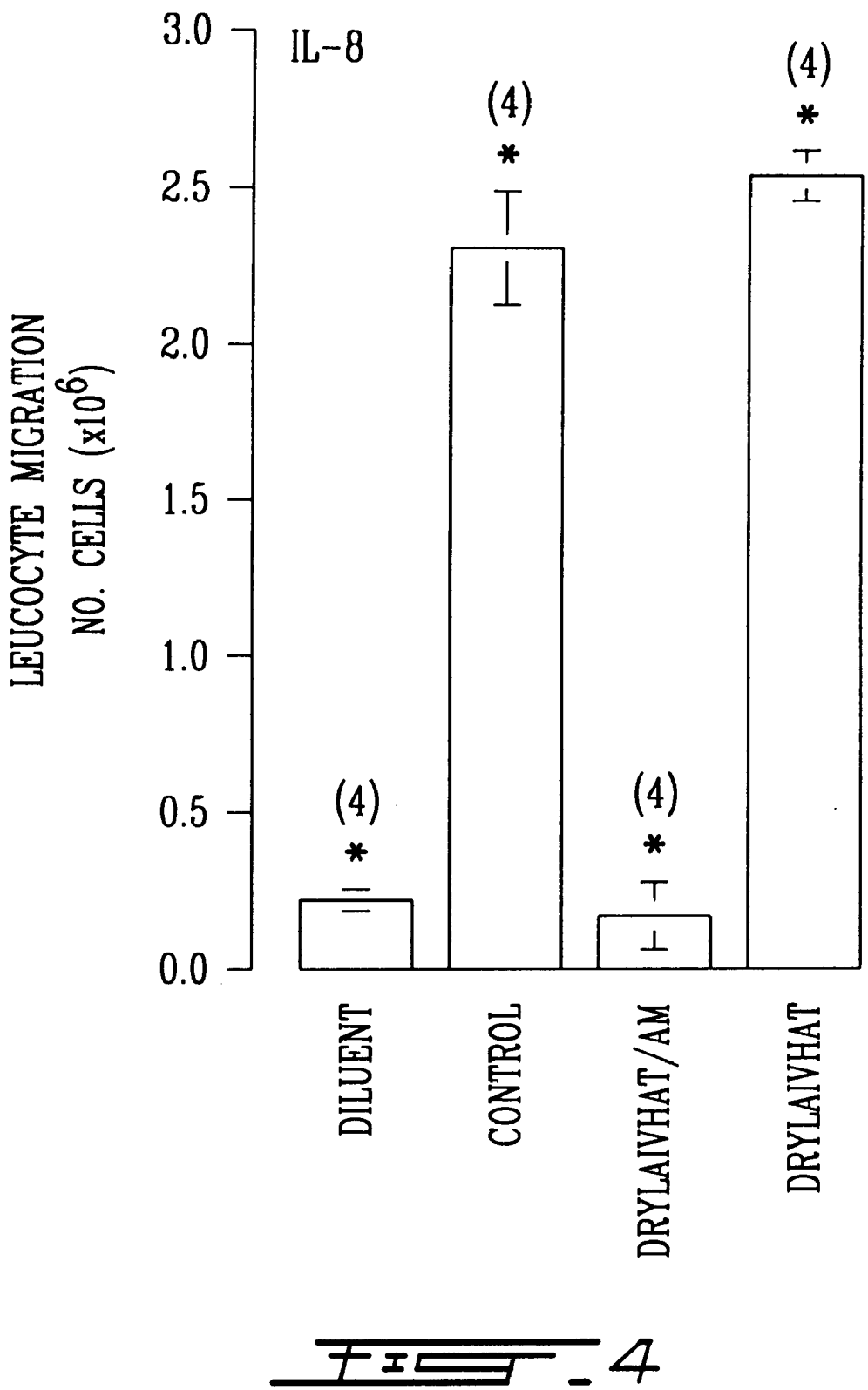
FIG. 4 illustrates the effects of IL-8RA derived peptides (DRYLAIVHAT/AM) on the IL-8-induced leukocyte migration into the mouse air pouch. IL-8 was used at 1 µg.

In FIG. 4, the peak increase in leukocyte migration induced by IL-8 is shown. The peptides (100 μg) (native or transformed) were injected intravenously in the tails of the BALBC mice one hour prior to IL-8 injection. The basal cell number was $0.25 \times 10^6$ cells and the increases represent the differences between the basal and the peak levels of the leukocytes collected two and a half hours after IL-8 stimulation. The data represent the mean ±SEM of the number of experiments indicated in parenthesis.

On the other hand, the injection of native peptides was without any detectable inhibitory effects on cell migration.

The use of this new generation of transformed peptides extends beyond the inhibition of single chemokines since the DRY region found in this peptide is common to a large number of chemotactic factors. The fact that this peptide was able to block the action of several chemotactic agents and chemokines makes it very likely that it can be used as a new form of anti-inflammatory agent. This suggestion is based on the fact that this peptide inhibited both calcium mobilization and in vivo leukocyte migration. The in vivo assays clearly demonstrate that the peptide, once transformed, is protected and can reach the target cells and block one of the major in vivo actions of the chemokines, leukocyte migration.

The present invention will be more readily understood by referring to the following examples which are given to illustrate the invention rather than to limit its scope.

EXAMPLE I

Development of Therapeutic Agents

The use of such transformation techniques on peptides and other, small molecular weight molecules can be of great help to the development of a new generation of therapeutic drugs composed of intracellular agonists or antagonists.

These therapeutic drugs would consist essentially of small peptides that antagonize intracellular signal transduction pathways.

Also these therapeutic drugs could be used in the treatment of arthritis, auto-immune diseases and hypersensitivity, inflammatory diseases, bacterial and viral infections, allergic reactions, neurological disorders and cancer.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 g. When a liquid carrier is used, the preparation will be in the form of a syrup, emulsion, soft gelatin capsule, sterile injectable liquid such as an ampoule or nonaqueous liquid suspensions.

AM-peptides may be administered topically, that is by non-systemic administration. This includes the application of the peptides externally to the epidermis or the buccal cavity and the instillation of such a peptide in the ear, eye and nose such that the peptide does not significantly enter the blood stream. In contrast, systemic administration refers to oral, intravenous, intraperitoneal and intramuscular administration.

Formulation suitable for topical administration include liquid or semi-liquid preparations suitable for penetration through the skin to the site of inflammation such as lotions, evens, ointments or pastes, and drops suitable for the administration to the eye, ear or noise. The active ingredient may comprise, for topical administration, from 0.001% to 10% W/W, and more preferably from 1% to 2% by weight of the formulation.

AM-peptides can be administered parentally, that is by intravenous, intramuscular, subcutaneous, intranasal, intrarectal, intravaginal administration.

For methods of use disclosed herein for the peptides in the AM form, the daily oral dosage regimen will preferably be form about 0.01 to about 80 mg/Kg of total body weight. The daily parenteral dosage regimen about 0.001 to about 80 mg/kg of total body weight. The daily topical dose regimen will be from 0.1 mg to 150 mg, administration one to four, preferably 2 to 3 times daily.

It will also be recognized by one of skill in the art that the optimal quantity, spacing of individual dosages of a peptide in the AM form will be determined by the nature and extent of the condition being treated, the form, route and site of administration, and the particular patient being treated, and that such optimum can be determined by conventional techniques. It will also be appreciated by one of skill in the art that the optimal cause of treatment i.e., the number of doses of a AM-peptide given per day for a defined number of days, can be ascertained by those skilled in the art using conventional course of treatment determination tests.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features herein before set forth, and as follows in the scope of the appended claims.

What is claimed is:

1. A hydrophobic membrane permeable peptide ranging from 6–15 amino acids which corresponds to a transmembrane or intracellular region of an interleukin-8 protein, wherein said peptide is in a transient modified inactive form for entering into a cell without disrupting the cell membrane, whereby primary amine groups of said peptide are modified to acetamides, and carboxylic acid and alcohol groups of said peptide are modified to acetoxymethyl esters, whereupon entering the cell, intracellular esterases cleave the acetoxymethyl moiety of said acetoxymethyl esters thereby converting said transient modified inactive form of said peptide to the original active form.

2. A pharmaceutical composition comprising an anti-inflammatory amount of the peptide defined in claim 1 in association with a pharmaceutically acceptable carrier.

3. A method of treating an inflammatory condition selected from the group consisting of inflammation, arthritis, auto-immune diseases, and hypersensitivity, which comprises administering a suitable amount of the pharmaceutical composition defined in claim 2.

* * * * *